United States Patent [19]

Pellett et al.

[11] Plant 5,053

[45] May 17, 1983

[54] RED MAPLE TREE

[75] Inventors: Harold M. Pellett, Mound; Leon C. Snyder, Excelsior, both of Minn.

[73] Assignee: University of Minnesota, Minneapolis, Minn.

[21] Appl. No.: 275,944

[22] Filed: Jun. 22, 1981

[51] Int. Cl.[3] ..... A01H 5/12

[52] U.S. Cl. ..... Plt./51

[58] Field of Search ..... Plt./51

*Primary Examiner*—Robert E. Bagwill

*Attorney, Agent, or Firm*—Merchant, Gould, Smith, Edell, Welter & Schmidt

[57] ABSTRACT

A red maple tree which exhibits a rapid, vigorous, and well-branched growth and well-rounded oval crown, which is seedless, has early autumn maturity and excellent winter hardiness in northern climates, and fall color better than average for the species.

5 Drawing Figures

ORIGIN OF THE CULTIVAR

The present invention relates to a new and distinct variety of red maple tree, *Acer rubrum.* The new variety or cultivar was discovered by us in a cultivated plot of *Acer rubrum* seedlings grown at the University of Minnesota Horticultural Research Center, located in Carver County near Excelsior, Minn.

*Acer rubrum* is native in the United States from Florida to southern Canada. However, selected cultivars available in the nursery trade and having good autumn leaf color are not reliably hardy in northern states and generally suffer winter injury in the form of tip die-back of branches. The autumn leaf color of native stands of red maple varies considerably from yellow to bright red, but native trees which are hardy in northern states generally do not have the good red fall leaf color desirable for commercially saleable red maple shade trees, or do not usually color early enough in the autumn before frost damage.

The plot of seedlings in which the present variety was discovered were grown from open pollinated seed obtained from a native population of *Acer rubrum* growing near Floodwood, Minn. The particular female parent tree from which the seed was collected for the plot of seedlings from which the present variety was selected had an excellent bright red fall color.

In the plot containing this variety, our attention was focused on this particular specimen which exhibited distinguishing and valuable characteristics, including excellent crown form, early autumn maturity, and winter hardiness in our northern climate, an absence of seeds or fruit, vigorous growth, and fall color better than average for the species. The present variety was carefully observed for several years, and the continued observation and testing have convinced us that the cultivar of this particular seedling is a new and improved variety as indicated by the following unique combination of qualities or characteristics which distinguish this variety from all other varieties of red maple trees known to us.

SUMMARY OF CHARACTERISTICS

The present variety has been named "Northwood" and will soon be introduced to the nursery trade by authorization of the University of Minnesota. Its unique combination of characteristics are as follows:

(1) Excellent crown form. The present variety produces a tree with a full, spreading and well-shaped crown form particularly desirable as a landscape shade tree, in comparison with other known cultivars or specimens of *Acer rubrum.* The well-shaped crown growth permits propagation of saleable size specimens in the nursery with a minimum of pruning or training in comparison to other known comparable varieties of red maple.

(2) Early fall maturity and winter hardiness. The present variety matures earlier in the autumn in comparison with other known varieties of *Acer rubrum,* with its leaves coloring in the autumn at a date earlier than other known specimens or varieties grown in the same area. Such early annual autumn maturity contributes to the winter hardiness of the present variety in Minnesota and other northern states of similar climate.

(3) Good fall leaf color. The present variety exhibits a bright red autumn coloring of its leaves which is better or more red than average in comparison to other known varieites of *Acer rubrum.*

(4) Vigorous growth. The present variety exhibits fast growth which is more vigorous than most varieties of red maple known to us, and specimens propagated therefrom reach a saleable size earlier than other comparable varieties of *Acer rubrum.*

(5) Seedless. The present variety has staminate flowers only and therefore produces no seed nor fruit.

ASEXUAL REPRODUCTION

The present variety has been asexually reproduced by means of grafting budding stock at the University of Minnesota Horticultural Research Center, Excelsior, Minn., and also by Bailey Nurseries, Inc., 1325 Bailey Road, Newport, Minn. Such asexual reproduction confirms the above-stated characteristics and qualities of the variety are true to form and consistent through seeding propagation.

SUMMARY OF THE CULTIVAR

The accompanying drawings comprise photographs showing characteristics of this new variety. The photographs were taken of a specimen of the variety growing in the aforesaid University of Minnesota Horticultural Research Center at Excelsior, Minn. The photographs depict features or characteristics of the present variety as true as reasonably possible.

FIG. 2 was taken at a time of drought stress, and fall foliage color is more typically that of FIG. 5.

The following is a detailed description or specification of the present variety. Color references relate to *The Royal Horticultural Society Colour Chart,* 1966 edition, noted herein as RHS, except color terms of ordinary dictionary meaning as may occasionally be used.

Parentage: The present variety was produced from a seedling of open pollinated seed obtained from an unnamed variety of *Acer rubrum* growing in a native population of trees near Floodwood, Minn.

Propagation: The present variety has been asexually reproduced by the grafting of bud stock and has held the distinguishing characteristics through succeeding propagations. The locality where the present variety has been primarily grown and observed is the University of Minnesota Horticultural Research Center near Excelsior, Minn.

Figure 2:
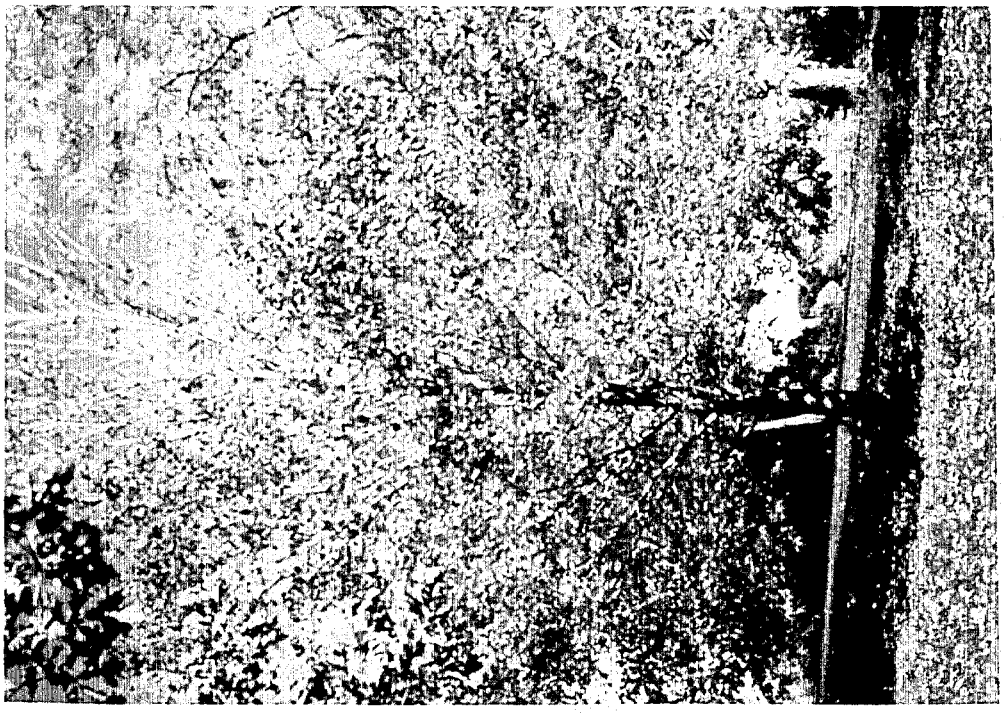
FIG. 2 is a color photograph showing the form of the tree in early autumn and the color of the foliage at the initial fall coloring stage.
Figure 1:
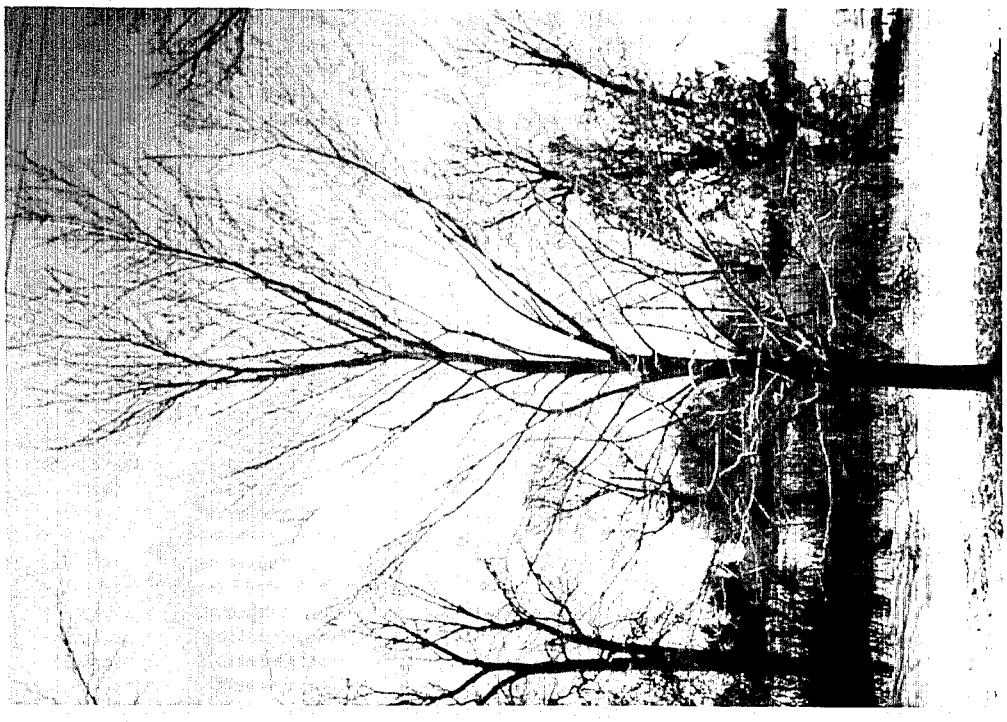
FIG. 1 is a photograph showing the variety defoliated in winter and depicting the general form of the tree and the excellent crown formed thereby.
Figure 3:
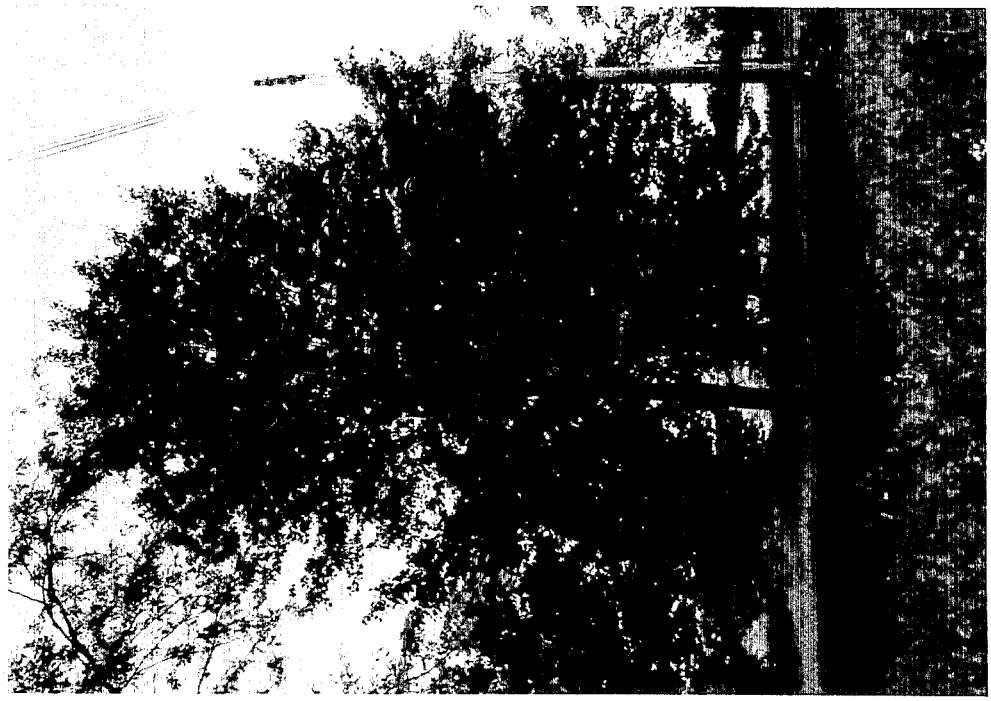
FIG. 3 is a color photograph showing the form of the tree at the full green leaf stage in early June.
Figure 4:
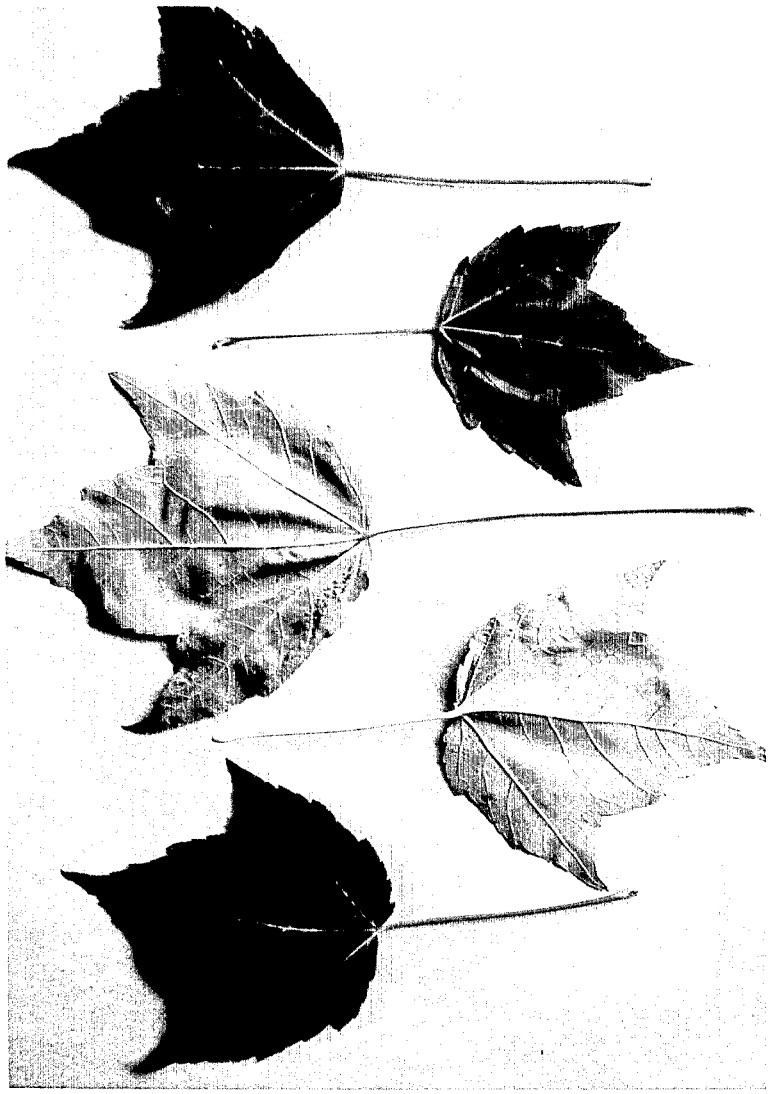
FIG. 4 is a color photograph showing a selection of leaves of the variety, some showing the upper side and some showing the lower side of the leaves.
Figure 5:
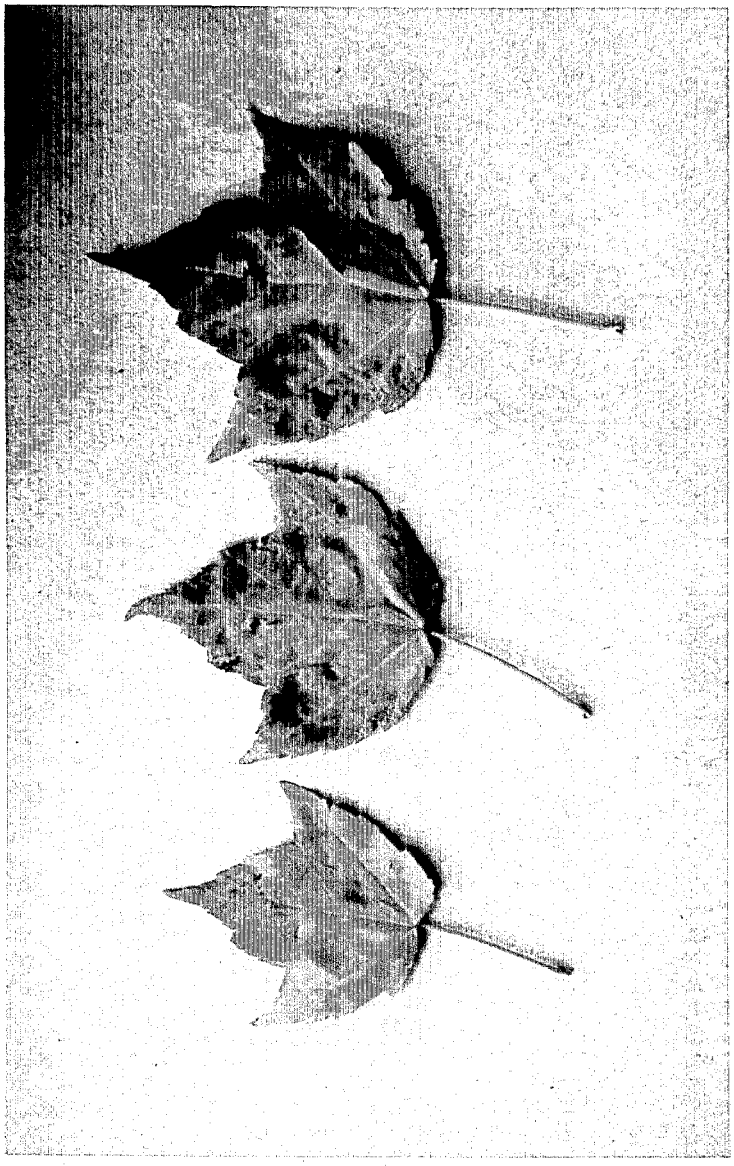
FIG. 5 is a color photograph showing a selection of leaves of different sizes and depicting the peak fall foliage color.

Tree:

*Form.*—The present variety exhibits a form with a full, spreading and well-rounded oval crown. It is more vigorous and faster growing than other common or comparable commercial varieties of *Acer rubrum* grown in the same Minnesota and similar northern climates. The present variety branches freely and produces a well-shaped tree ready for commercial sale at an early date and with a minimum of pruning or nursery training, in comparison with other known varieties of the species grown in such northern climates. The typical shape of this variety is illustrated in FIGS. 1–3. The original tree of this variety is now 25 years of age and is approximately 9 meters in height with a well-rounded oval crown.

*Trunk.*—Moderately stout. Moderately rough.

*Branches.*—Forming approximately 45° angles with trunk. Winter color of one-year stem corresponds to RHS #175A.

Lenticels.—Average size and density.

*Foliage.*—Three-lobed leaves with truncate to cordate bases. Serrate margins with approximately 2.5 serrations/cm. Leaf blades: Larger leaves average 11 cm. in width (range of 9.2 to 12.8 cm.) and 10 cm. (range of 7.5 to 11.7 cm.) in length. Overall leaf blade average of 7.3 cm. in width (range of 2.3 to 13.0 cm.) and 8 cm. (range of 5.0 to 11.3 cm.) in length. Petioles: Petioles on larger leaves average 7.2 cm. (range of 3.0 to 10.0 cm.). Petioles from overall sample average 6.3 cm. (range of 2.9 to 10.5 cm.). Summer leaf color: Upper side of leaf blade is RHS #147A and glabrous. Lower side of leaf blade is RHS #191B and glaucous, with scattered hairs. There appears to be slight variation in the upper side of the leaf blade color, depending upon season and natural variation. Fall leaf color: The variety is subject to some variation in fall leaf color, depending upon factors such as drought and seasonal climatic conditions. Under average conditions, the peak color is closest to RHS #46A. This color observation was made on Oct. 3, 1982, at the University of Minnesota Horticultural Research Center near Excelsior, Minn.

*Flower buds.*—Size: 3 mm. long. Shape: Roundish obovate. Color: Bud scales are RHS #187A.

*Flowers.*—Date of bloom: Typically mid to late April in the Minnesota locality where grown as noted above. Quantity: Average. Overall size: Up to 1.3 cm. from base of pedicel to anthers. Sex: Staminate. The present variety has no female flower parts and produces no seed or fruits. Color: Overall effect of corolla is RHS #50B. Petals: 5 petals, 2 mm. long, oblong linear.

*Seeds.*—None, as determined from observation of mature tree which is 25 years old. The present variety is seedless because it has no female flower parts to produce fruit.

*General characteristics.*—As compared with other common and commercial varieties of red maple trees grown in northern climates and known to us, the present variety exhibits excellent crown form, a rapid vigorous growth, early autumn maturity, and excellent winter hardiness, a better than average red autumn leaf color, and is also seedless.

I claim:

1. A new and distinct variety of red maple tree, substantially as shown and described herein, characterized particularly as to novelty by the unique combination of a rapid vigorous growth, a well-rounded full spreading and well-branched oval crown form, early autumn maturity and excellent winter hardiness, a fall red color better than average for the species, and an absence of seeds.

* * * * *